Sept. 16, 1952 M. L. WHISLER Plant Pat. 1,134
ROSE PLANT
Filed Sept. 26, 1951
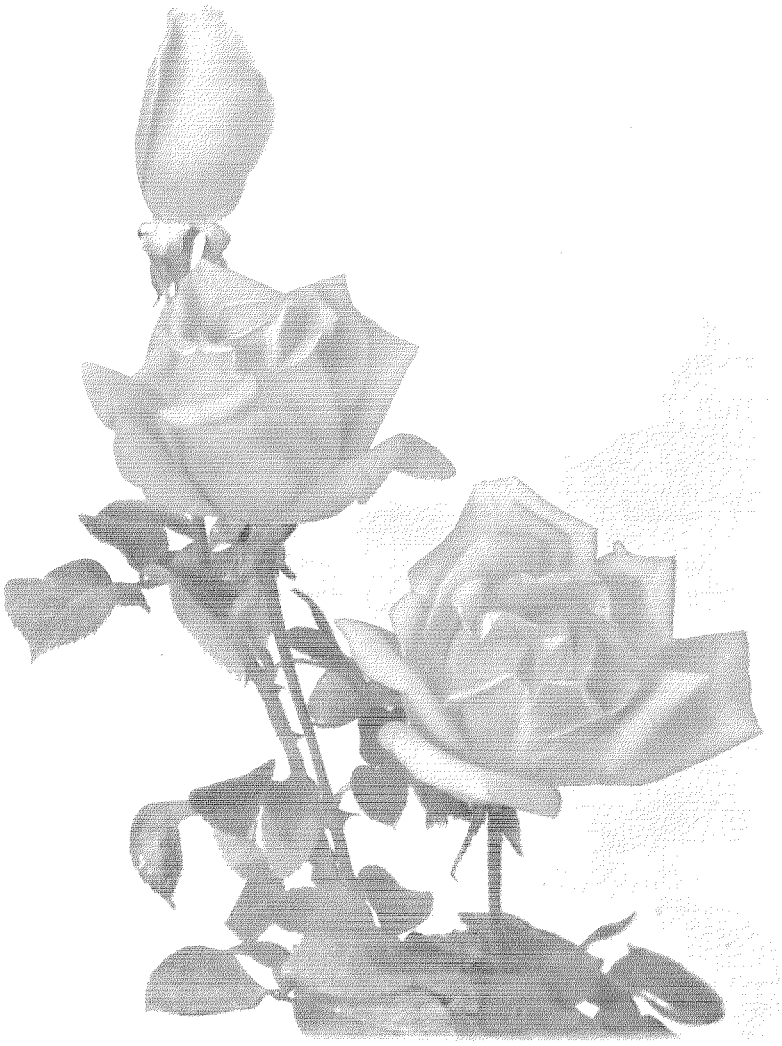
Inventor.
M. L. Whisler
By: Cobb & Cobb
Attorneys.

UNITED STATES PATENT OFFICE 1,134

ROSE PLANT

Milton L. Whisler, Van Nuys, Calif., assignor to Germain's, Inc., Van Nuys, Calif., a corporation of California Application September 26, 1951, Serial No. 248,296

1 Claim. (Cl. 47—61)

The present invention relates to a new and distinct variety of rose plant of the hybrid tea class, originated by me by crossing an unnamed and unpatented seedling × the variety commercially known as "The Doctor" (unpatented).

As the result of this cross, I have produced a new variety which is substantially different from its parents as well as from other varieties of this class, but which resembles the well-known variety "Charlotte Armstrong" (Plant Patent No. 455) more than any other, yet is distinctly different therefrom.

The primary features of novelty and distinctiveness of the new variety are evidenced by its bushy and branching habits of growth, by the unusually large flower petals and length of the buds, and by the abundance of its blooms of Rose Madder general color tonality.

Asexual reproduction of this new variety by cuttings, grafting and budding at Van Nuys, California, shows that the foregoing characteristics come true and are established and transmitted through succeeding propagations.

The accompanying drawing shows specimens of the flowers and foliage of the new variety in different stages of development.

The following is a detailed description of the new variety, with color terminology in accordance with the Horticultural Color Chart of the British Color Council, except where general color terms of ordinary dictionary significance are obvious:

Type: Half hardy; bush; outdoor; seedling; for cut flowers and for garden decoration.

Class: Hybrid tea.

Breeding: Seedling.

*Seed parent.*—An unnamed seedling.

*Pollen parent.*—"The Doctor."

Propagation: Holds its distinguishing characteristics through succeeding propagations by cuttings, grafting and budding.

*Flower*

Locality where grown and observed: Van Nuys, California.

Flowers borne: Singly to stem; on normal strength, medium length stems.

Quantity of bloom: Abundant; outdoors.

Continuity: Continuous.

Fragrance: Moderate; sweetbriar.

Bud:

*Peduncle.*—Medium length; medium thickness; bending; medium erect; light yellowish green; almost smooth; few red-brown hairs.

*Before calyx breaks.*—Size—large. Form—long; pointed; with a conspicuous neck; without foliaceous appendages on the surface of the bud; without foliaceous parts extending beyond the tip of the bud. Color—light grey-green.

*As calyx breaks.*—Color—Cardinal Red, Plate 822/3.

*As first petal opens.*—Size—large. Form—long; pointed. Color—outside: Cardinal Red, Plate 822/3; inside: Cardinal Red, Plate 822.

*Opening.*—Opens up well.

Bloom:

*Size, when fully open.*—Large; 5 inches to 5½ inches.

*Petalage.*—Semi-double; from 25 to 30 petals, arranged irregularly.

*Form.*—High center; becoming open; petals being at first loosely rolled outward; becoming later, at maturity, very loosely rolled outward.

Petals: Thin; soft; with inside and outside satiny.

*Shape.*—Outside—round; with two notches. Intermediate—obovate; with two notches.

This description of a newly opened flower was made from a rose grown outdoors in the month of August, at Van Nuys, California:

*Color.*—Outside petal—outside surface: Neyron Rose, Plate 623/1; inside surface: Rose Madder, Plate 23/1. Intermediate petal—outside surface: Neyron Rose, Plate 623; inside surface: Rose Madder, Plate 23. Inner petal—outside surface: Neyron Rose, Plate 623/2; inside surface: Rose Madder, Plate 23/2.

This description was made from a rose that was open for three days outdoors in the month of August, at Van Nuys, California:

*Color.*—Outside petal—outside surface: Neyron Rose, Plate 623/1; inside surface: Rose Madder, Plate 23/1. Inside petal—outside surface: Neyron Rose, Plate 623/2; inside surface: Rose Madder, Plate 23/2.

*General color effect.*—Newly opened flower—Rose Madder, Plate 23/1. Three days open—Rose Madder, Plate 23/1.

*Behavior.*—Drop off cleanly.

*Flower longevity.*—On bush in garden—4 days in August. Cut roses, grown outdoors, kept at living room temperature—3 days in August.

*Reproductive organs*

Stamens: Many; arranged regularly about pistils.
Filaments: Long; most with anthers: Color—Straw Yellow, Plate 604.
Anthers: Medium size; open at various times. Color—Straw Yellow, Plate 604/2.
Pollen: Moderate abundance; lemon.
Pistils: Medium number.
Styles: Uneven; medium length; thin; bunched.
Stigma: White.
Ovaries: Some protruding from calyx.
Hips: Short; flat; with inconspicuous neck; green-grey; smooth; walls thin, dry.
Sepals: Permanent; long; recurved; grey-green.

*Plant*

Foliage:

*Leaves.*—Compound of five leaflets; normal abundance; medium size; moderately heavy; leathery.

*Leaflet.*—Shape—elliptic, with apex acute. Base—obtuse. Margin—doubly serrate.

*Color.*—Mature—upper surface: moderately dark green; under surface: light grey-green. Young—upper surface: normal grey-green. Under surface: light bronze-red.

*Rachis.*—Medium weight. Upper side—grooved; hairy. Under side—sparsely thorny.

*Stipules.*—Very short; medium width; with very short points turning out at an angle of 90°.

*Disease.*—Resistant to mildew.

Growth:

*Habit.*—Bushy; much branched.

*Growth.*—Moderate.

*Canes.*—Medium heavy.

*Main stems.*—Color—dull green. Thorns—many; medium length; with short, broad base. Prickles—few; grey-brown. Hairs—none.

*Branches.*—Color—grey-green. Thorns—many; medium length; straight; with short, round base. Prickles—few; reddish. Hairs—none.

*New shoots.*—Color—dull green-bronze. Thorns—many; long; straight; with narrow base. Prickles—several; reddish. Hairs—none.

I claim:

A new and distinct variety of rose plant of the hybrid tea class, substantially as herein shown and described, characterized as to novelty by its bushy and branching habits of growth, by the unusually large flower petals and length of the buds, and by the abundance of its blooms of Rose Madder general color tonality.

MILTON L. WHISLER.

No references cited.